(12) United States Patent
Rauf et al.

(10) Patent No.: US 11,452,708 B2
(45) Date of Patent: Sep. 27, 2022

(54) **DISCOVERY OF POTENT [ALPHA]-GLUCOSIDASE INHIBITORS FROM *HETEROPHRAGMA ADENOPHYLLUM***

(71) Applicant: KING ABDULAZIZ UNIVERSITY, Jeddah (SA)

(72) Inventors: Abdur Rauf, Jeddah (SA); Zafar Ali Shah, Jeddah (SA); Yasir Anwar, Jeddah (SA); Abdul Wadood, Jeddah (SA); Hani Mohammed Ali, Jeddah (SA); Abdurahman Labeed Almalki, Jeddah (SA); Khalid Mohammed S. Al-Ghamdi, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/169,666

(22) Filed: Feb. 8, 2021

(65) Prior Publication Data

US 2022/0249428 A1     Aug. 11, 2022

(51) Int. Cl.
| | |
|---|---|
| *A61K 31/352* | (2006.01) |
| *C07C 46/10* | (2006.01) |
| *C07D 311/94* | (2006.01) |
| *C07D 311/78* | (2006.01) |
| *C07C 67/58* | (2006.01) |
| *A61K 31/122* | (2006.01) |
| *A61K 31/216* | (2006.01) |

(52) U.S. Cl.
CPC .......... *A61K 31/352* (2013.01); *A61K 31/122* (2013.01); *A61K 31/216* (2013.01); *C07C 46/10* (2013.01); *C07C 67/58* (2013.01); *C07D 311/78* (2013.01); *C07D 311/94* (2013.01); *A61K 2236/13* (2013.01); *A61K 2236/15* (2013.01); *A61K 2236/17* (2013.01); *A61K 2236/31* (2013.01); *A61K 2236/333* (2013.01); *A61K 2236/35* (2013.01)

(58) Field of Classification Search
None
See application file for complete search history.

(56) References Cited

U.S. PATENT DOCUMENTS

| | | | |
|---|---|---|---|
| 6,117,887 A * | 9/2000 | Lum | A61K 31/445 514/319 |
| 2005/0043408 A1* | 2/2005 | Yeboah | A61P 3/10 514/567 |

OTHER PUBLICATIONS

Shah et al. Peshawaraquinone a Novel Naphthoquinone and a New Indanone from the stem of Heterophragma adenophyllum Seem, 2015, Rec. Nat. Prod. 9:2, pp. 169-174.*
Mahmoud et al., Phytochemical and biological overview of genus "Bignonia" (1969-2018), 2019, J Adv Biomed & Pharm Sci, 2: 83-97.*
Guerra et al., Interceptive Effect of Lapachol in Rats, 1999, Contraception, 60; 305-307.*

* cited by examiner

*Primary Examiner* — Terry A McKelvey
*Assistant Examiner* — Catheryne Chen
(74) *Attorney, Agent, or Firm* — WCF IP

(57) ABSTRACT

A family of α-glucosidase inhibitors are identified. Exemplary α-glucosidase inhibitors may be obtained from *Heterophragma adenophyllum* seem. The inhibitors are used to lower blood sugar levels and thus to treat diseases related to or characterized by high blood sugar, such as diabetes.

9 Claims, 3 Drawing Sheets

Figure 3A
Figure 3B
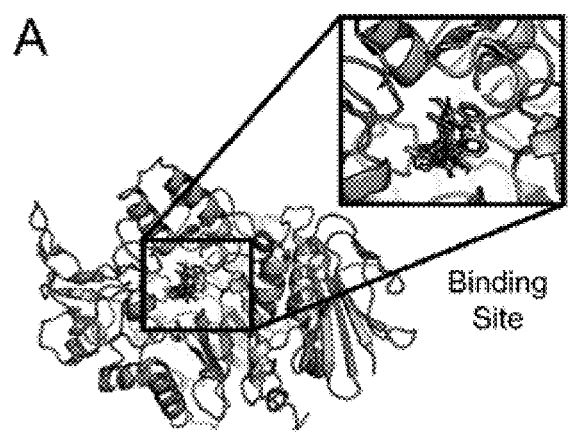
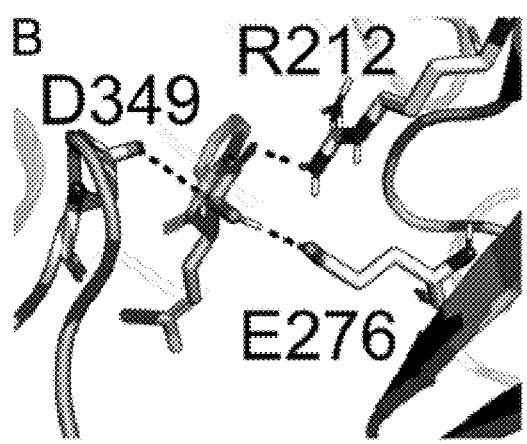
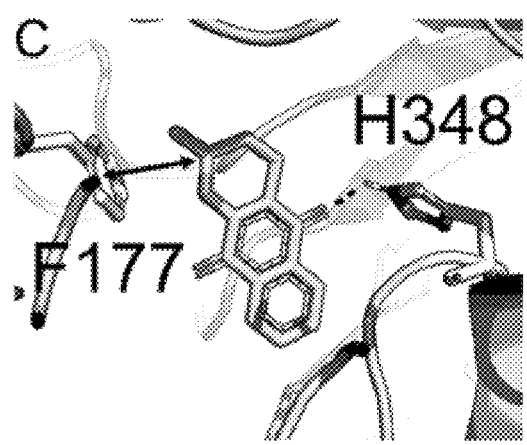
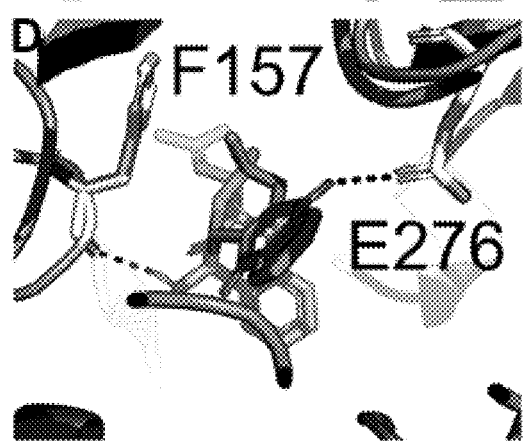
Figure 3C
Figure 3D

DISCOVERY OF POTENT [ALPHA]-GLUCOSIDASE INHIBITORS FROM *HETEROPHRAGMA ADENOPHYLLUM*

FIELD OF THE INVENTION

The invention generally relates to potent α-glucosidase inhibitors for use in the treatment of high blood sugar and related diseases such as diabetes.

BACKGROUND OF THE INVENTION

*Heterophragma adenophyllum* is a flowering plant which is a member of the family Bignoniacea. It is distributed throughout South Africa, Southeast Asia and one representative species is cultivated in Pakistan [1]. Its height ranges from 15-20 cm and the leaflets are from 3-6 cm in length and its flowers, which occur in panicles, are pale yellow in color. *H. adenophyllum* flowers usually remain open at night and close in daytime. The plant produces long fruits which hang from the branches like snakes. Its fruits are extensively used in traditional systems and oils extracted from the fruits are used for massage to ease muscular tension [1, 2]. According to folklore, various parts of H. adenophyllum have been used by local people for curing various ailments such as premature ejaculation. This plant is also documented for possessing various interesting pharmacological potentials such as anti-microbial and anti-diabetic properties, treatment of night emission and amenorrhea, as an antiseptic and for curing skin disease [1, 3].

*H. adenophyllum* is an important source of bioactive natural products, including various phytochemicals such as dehydro-α-lapchone, β-amyrin, lapachol, apchoneadenophylone, α-lapchoneadenophylone, dehydro-α-lapchone, dilapachone, dilapachone, tecomoquinone-I and β-sitosterol and dehydro-iso-α-lapachone, etc., as documented in literature [4]. The majority of species of the Bignoniacea family are known for the isolation of lapachol in bulk amounts. Lapachol and its diverse derivatives have been reported for their different biological properties, such as anti-carcinomic, anti-edemic, anti-ulcer, anti-inflammatory, viricidal, antimalarial, termiticidal and anti-abscess activity [5-10]. Biochemical parameters as well as anti-hypertensive activity of *H. adenophyllum* has been documented [11]. A steroidal fraction of leaf extract of *H. adenophyllum* possesses antimicrobial potential [12]. The bark and leaves of *H. adenophyllum* have been investigated for excellent antioxidant activity [13].

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

The present disclosure describes the isolation of bioactive compounds which bind to and inhibit the action of α-glucosidase. Uses of the compounds to inhibit the enzyme α-glucosidase, to stabilize and/or decrease blood sugar levels in subjects and to prevent and/or treat diabetes in subjects are encompassed. Exemplary compounds include but are not limited to phytochemicals such as lapachol, peshawaraquinone, an indanone derivative (Methyl 1,2-dihydroxy-2-(3-methylbut-2-enyl)-3-oxo-2, 3-dihydroxo-1H-indene-1-carboxylate), and α-lapachone. These and other compounds are isolated e.g., from *Heterophragma adenophyllum*. The exemplary phytochemicals described herein are advantageously less expensive and more readily available than currently marketed medicines. They exhibit less toxicity and are more active at lower doses than currently available drugs.

An aspect of the invention is to inhibit α-glucosidase in a subject by providing the subject with one or more chemicals suitable for the same (i.e., α-glucosidase inhibitors). The α-glucosidase inhibitors can be used in the treatment of type II diabetes, and other conditions.

In an embodiment of the invention α-glucosidase is inhibited (e.g., activity is reduced or blocked) by contacting the α-glucosidase with a compound of Formula I:

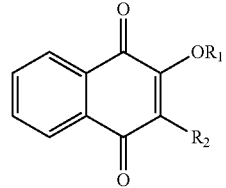

Formula I wherein R1 is H or, together with R2, forms part of a 6-carbon monocyclic ring structure or a multicyclic ring structure, and wherein if R2 is not part of a ring structure, then R2 is a C1-5 carbon chain which is saturated or unsaturated, substituted or unsubstituted and branched or unbranched. In another embodiment of the invention α-glucosidase is inhibited by contacting the α-glucosidase with a compound of Formula II:

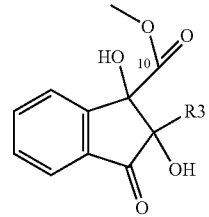

Formula II wherein R3 is a C1-5 carbon chain, which is saturated or unsaturated, substituted or unsubstituted, and branched or unbranched.

In some aspects, what is provided is a method of inhibiting α-glucosidase, comprising contacting the α-glucosidase with one or more of a compound of Formula I:

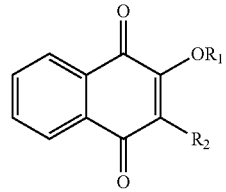

Formula I wherein R1 is H or, together with R2, forms part of a 6-carbon monocyclic ring structure or a multicyclic ring structure; and wherein if R2 is not part of a ring structure, then R2 is a C1-5 carbon chain which is saturated or unsaturated, substituted or unsubstituted, and branched or unbranched; and a compound of Formula II:

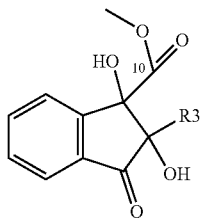

Formula II wherein R3 is a C1-5 carbon chain, which is saturated or unsaturated, substituted or unsubstituted, and branched or unbranched. In some aspects, the compound is one or more of lapachol, peshawaraquinone, an indanone derivative (Methyl 1,2-dihydroxy-2-(3-methylbut-2-enyl)-3-oxo-2,3-dihydroxo-1H-indene-1-carboxylate), and α-lapachone.

Further aspects provide a method of stabilizing or decreasing blood sugar levels in a subject in need thereof, comprising administering a therapeutically effective amount of one or more of a compound of Formula I:

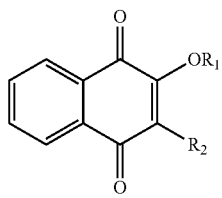

Formula I wherein R1 is H or, together with R2, forms part of a 6-carbon monocyclic ring structure or a multicyclic ring structure; and wherein if R2 is not part of a ring structure, then R2 is a C1-5 carbon chain which is saturated or unsaturated, substituted or unsubstituted, and branched or unbranched; and a compound of Formula II:

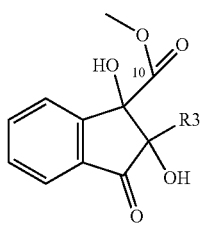

Formula II wherein R3 is a C1-5 carbon chain, which is saturated or unsaturated, substituted or unsubstituted, and branched or unbranched. In some aspects, the at least one compound is lapachol, peshawaraquinone, an indanone derivative, or α-lapachone. In further aspects, the therapeutically effective amount is 0.2 mM to 0.00625 mM. In additional aspects, the step of administering is performed orally or by injection.

In some aspects, what is provided is a method of treating diabetes in a subject in need thereof, comprising administering to a subject in need thereof a therapeutically effective amount of one or more of a compound of Formula I:

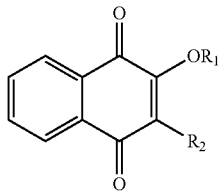

Formula I wherein R1 is H or, together with R2, forms part of a 6-carbon monocyclic ring structure or a multicyclic ring structure; and wherein if R2 is not part of a ring structure, then R2 is a C1-5 carbon chain which is saturated or unsaturated, substituted or unsubstituted, and branched or unbranched; and a compound of Formula II:

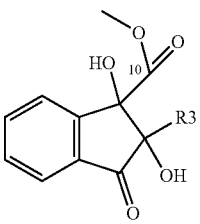

Formula II wherein R3 is a C1-5 carbon chain, which is saturated or unsaturated, substituted or unsubstituted, and branched or unbranched. In some aspects, the at least one compound is lapachol, peshawaraquinone, an indanone derivative, or a-lapachone. In further aspects, the therapeutically effective amount is 0.2 mM to 0.00625 mM. In additional aspects, the step of administering is performed orally or by injection. In yet further aspects, the diabetes is type I diabetes, type II diabetes, secondary diabetes, gestational diabetes, or a combination of two or more of these.

Also provided is a method of making lapachol, peshawaraquinone, an indanone derivative, and/or α-lapachone, comprising: harvesting *Heterophragma adenophyllum* seem, and extracting one or more of lapachol, peshawaraquinone, an indanone derivative, and α-lapachone from heartwood and/or roots of harvested *H. adenophyllum* seem.

BRIEF DESCRIPTION OF THE DRAWINGS

FIG. 3A-D. The ligand-protein interaction (LPI) profile against the α-glucosidase enzyme for phytochemicals isolated from stem heartwood (A). The α-glucosidase enzyme's surface association with phytochemicals at the binding site. The binding mode of the most potent compound (B) for compound 1, (C) compound 4 and (D) for Compound 2.

DETAILED DESCRIPTION

Bioactive compounds are provided herein, as are methods of their use e.g., to inhibit the enzyme α-glucosidase, to stabilize and/or decrease blood sugar levels in subjects and to prevent and/or treat diabetes (particularly type II diabetes) in subjects.

In some aspects, the compounds have or comprise the general structure shown in Formula I:

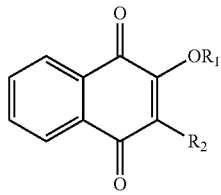

Formula I where R1 is H or, together with R2, forms part of a 6-carbon monocyclic ring structure or a multicyclic ring structure.

In some aspects, the 6-carbon monocyclic ring may i) contain one or more functional groups attached to the ring at any position e.g., one or more C1-C5 carbon chains, which may be branched or unbranched, and substituted or unsubstituted. If substituted, one or more hydrogen atoms of a chain may be replaced by an atom such as O, S, halogen, etc. In addition, a chain may or may not have one or more functional groups attached thereto at any position, e.g., functional groups such as: one or more C1-C5 carbon chains, which may be substituted or unsubstituted, branched or unbranched; hydroxyl; carboxyl; etc.

In some aspects, the multicyclic ring structure comprises e.g., from about 2 to about 5 rings in total, for example conjoined 5- and/or 6-membered rings which may be saturated or unsaturated (e.g., pentyl, hexyl, benzyl, etc.) and substituted or unsubstituted. If substituted, then one or more hydrogen atoms within a ring may be replaced by an atom such as O, S, halogen, etc. In addition, a ring may or may not have one or more functional groups attached thereto at any position, e.g., functional groups such as: one or more C1-C5 carbon chains, which may be substituted or unsubstituted, branched or unbranched; hydroxyl; carboxyl; etc.

If R2 is not part of a ring structure, then R2 is typically a C1-C5 carbon chain, which may be saturated or unsaturated, substituted or unsubstituted, and branched or unbranched.

In other aspects, the compounds have or comprise the general structure shown in Formula II:

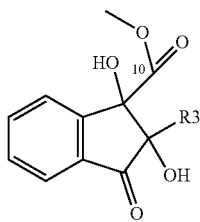

Formula II where R3 is a C1-5 carbon chain, which may be saturated or unsaturated, substituted or unsubstituted, and branched or unbranched.

In some aspects, the compounds interact principally with and/or bind to one or more of residues Asp349, Glu276, Phe177, Phe157, His348 and Arg212 of α-glucosidase.

Figure 1:
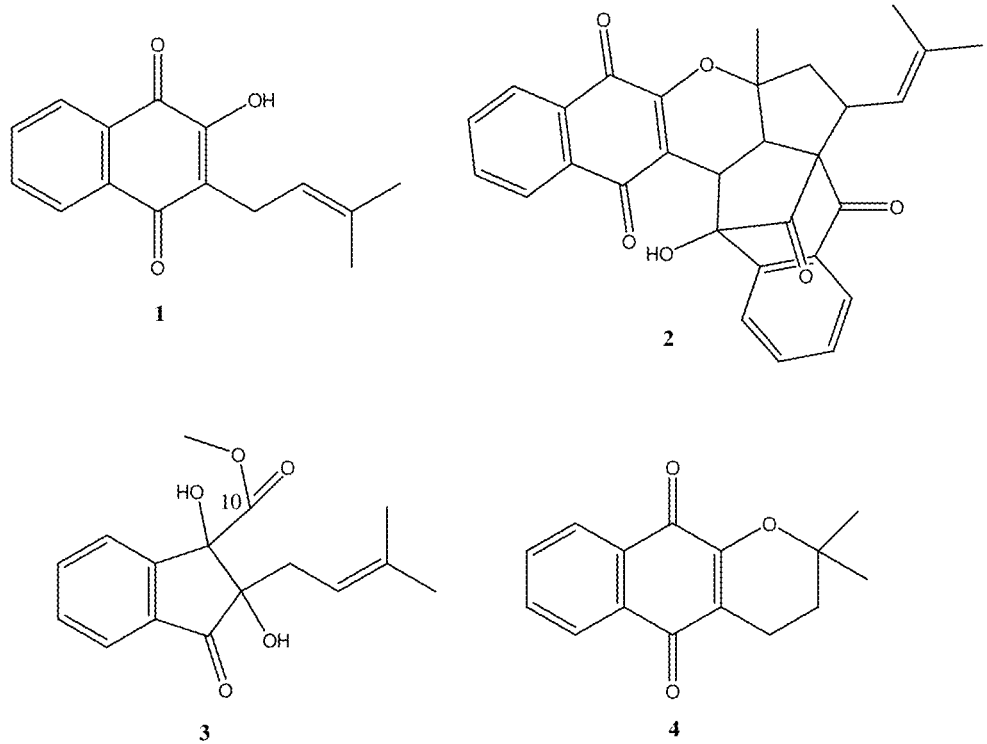
FIG. 1: Structure of phytochemicals (1-4) isolated from stem heartwood of *Heterophragma adenophyllum* Seem.

In some aspects, the compounds are the exemplary compounds lapachol (1), peshawaraquinone (2), and α-lapachone (4), as depicted in FIG. 1, which are examples of compounds of Formula I; or the indanone derivative (3) which is an example of Formula II.

PREPARATION

In some aspects, the compounds disclosed herein are chemically synthesized using techniques known to those of skill in the art.

In other aspects, the compounds described herein are derived from natural sources. For example, exemplary compounds 1-4 are generally prepared by first properly identifying and harvesting a plant or plants belonging to the species *Heterophragma adenophyllum*. In some aspects, the *H. adenophyllum* related species are reported with presence of peshawaraquinone (2) such as *Fernandoa adenophylla* (Wall. ex G. Don) Steenis.

Generally, the plants are harvested at maturity, i.e., the stem and stalks of the plants used to bear the flowers and fruits seasonally may be collected. Generally, the entire plant, including roots, stalks, stems, flowers, fruit, etc. are harvested. However, the parts of the plant that are generally used for production of the compounds include the heartwood of the stems and stalks.

Typically, the harvested plants or the parts of the plants that will be used to prepare the compounds, are shade dried (room temperature) avoiding harsh drying conditions. The dried plant material is then ground or macerated in any convenient and suitable manner, to form ground particulate plant material, which may be e.g., a coarse or fine powder. In some aspects, the ground plant material may be filtered and/or sieved and/or centrifuged to remove larger particles, prior to extraction. The steps of grinding may be performed in the cold (e.g., at from about 0-10° C., such as about 0, 1, 2, 3, 4, 5, 6, 7, 8, 9, or 10° C.).

The compounds of interest are typically separated from the ground plant (1Kg) material by cold extraction with a suitable solvent. Suitable solvents for this purpose include methanol to obtain a concentrated crude extract (80 g). The acquired crude extract is further fractionized with various organic solvents based on polarity and concentrated to yield n-hexane, (2.74 g), dichloromethane (5.23 g), ethyl acetate (6.53 g) and methanolic (10.91 g) fractions. The methanolic fraction (12 g) may be subjected to normal phase column chromatography (CC) on silica gel (70-230 mesh) using chloroform: methanol as an eluent, resulting in further sub-fractions (ZF1-200). These may be compiled into 10 major fractions based on their comparative TLC profiles and may further be purified by gel filtration ((SephadexR LH-20), silica gel, 400 mesh) and TLC using suitable solvent systems. Sub-fraction ZF-4 resulted in isolation of compound 3 (80 mg). The sub-fraction ZF-8 may be subjected to pencil column chromatography using chloroform and methanol as the eluent to afford compound 4 (71 mg). The fraction ZF-14 may be subjected to column chromatography using chloroform and methanol (8:2 to 7:1) to give compound 1 (5 mg). On the other hand, sub-fraction ZF-17 may be subjected to column chromatography using chloroform and methanol (6:2) as an eluent to yield compounds 2 (4 mg) and 3 (82 mg). All isolated compounds may further be purified through washing with n-hexane. In some aspects, steps of filtering and/or sieving and/or centrifuging may be added if unwanted precipitates form.

Individual compounds are generally isolated from each other and other compounds present in an extract (i.e., purified from the initial extract(s)) using a separation technique such as, for example, column chromatography (CC) based on silica gel. As a non-limiting example, the compounds may be individually eluted by using chloroform: methanol (90:10) as a solvent system. Column fractions may be further processed to remove impurities, e.g., by washing one or more times with one or more non-polar solvents such as hexane, heptane. Other methods of separating and purification of the compounds include but are not limited to: recrystallization and filtering may be used if necessary, to remove unwanted precipitates.

Methods of verifying the identity and purity level of the compounds are known in the art and include, for example, chromatography, UV, IR, $^1$H & $^{13}$C NMR, NOSEY, COSY, ROSEY, HSQC, HMBC & MS. Compounds that are formulated into dosage forms as described below are generally substantially purified to a level of a least about 90% -100% purity, and usually about 90% -100% purity, e.g., about 90, 91, 92, 93, 94, 95, 96, 97, 98, 99 or even 100% free of other compounds, excluding solvent molecules, ions, etc.

Methods of making the compounds disclosed herein are also encompassed, e.g., by extracting them from the heartwood of *H. adenophyllum* seem.

COMPOSITIONS AND USES

Once they have been synthesized and/or isolated and verified, the compounds described herein are generally formulated for delivery (administration) as or in a pharmaceutical or "health care" composition. Further, since the compounds are from "natural sources", the pharmaceutical or health care compositions may be, in some aspects, be termed "nutritional compositions" or "nutraceuticals". The "pharmaceutical compositions" disclosed herein encompass all such designations.

Prior to formulation, the compounds may be converted into a form suitable for manufacturing a particular medicament form. For example, a compound may be concentrated to obtain a concentrated liquid preparation, and/or dried or lyophilized (e.g., with or without additional pulverization), and/or crystallized, etc. before being processed into a desired dosage form.

The pharmaceutical/health care compositions disclosed herein generally comprise at least one of the disclosed compounds (as shown in FIG. 1, or an active derivative thereof as described elsewhere), i.e., one or more than one (a plurality) of different compounds (e.g., 2 or more such as 2, 3 or 4) may be included in a single formulation. The present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g., lyophilized forms of the compounds), as are emulsified preparations. Chewable forms and dissolvable forms (e.g., to dissolve in a drink) are also encompassed, especially for children. In some aspects, the liquid formulations are aqueous or oil-based suspensions or solutions. In some aspects, the active ingredients are mixed with excipients which are pharmaceutically acceptable and compatible with the active ingredients, e.g., pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of compound in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as Tween® 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The compounds (phytochemicals) disclosed herein are useful for a variety of purposes, including but not limited to: to inhibit the α-glucosidase enzyme in any context, e.g., in vitro (such as in a laboratory) or in vivo, such as in a living subject; to stabilize and/or lower blood sugar levels in subjects in need thereof; and/or to prevent or treat any type of diabetes, including primary diabetes (diabetes type I and type II) and secondary diabetes, as well as associated conditions that typically precede the development of full-blown diabetes, e.g., insulin resistance (metabolic syndrome) and/or diabetes Type II or simply higher than normal blood glucose levels, as determined by standard procedures used by medical professionals, e.g., physicians. Gestational diabetes which occurs during pregnancy, may also be treated. Any disease or condition characterized by high blood sugar can be treated by administration of the compounds.

Generally, subjects in need of stabilizing and/or lowering blood sugar levels include those with e.g., pre-diabetes and those with metabolic syndrome (also referred to as "insulin resistance") which is typically associated with obesity, as well as subjects with diabetes. Subjects with "prediabetes" have a higher-than-normal blood sugar level. The risk of prediabetes increases after age 45, if there is a family history of diabetes, in subjects with e.g., obstructive sleep apnea, and those who smoke. Such subjects may also have high blood pressure, low levels of high-density lipoprotein (HDL) cholesterol, and/or high levels of triglycerides, (silent) heart attacks, kidney damage, etc. each of which conditions may be improved or avoided when the compounds disclosed herein are administered to an afflicted subject. Generally, a combination of three or more of these conditions is often called metabolic syndrome.

Secondary diabetes is diabetes that results as a consequence of taking a medication that is not necessarily intended to treat diabetes, endocrine disease or hereditary disease. Examples include but are not limited to: pancreatic diabetes characterized by insulin deficiency following pancreatic diseases, such as pancreatitis and pancreatic cancer; endocrine diseases such as Cushing's syndrome and acromegaly; the use of steroids which induce hyperglycemia (orally, by injection, cutaneously and/or by inhalation); hereditary conditions with which diabetes is associated such as MODY and mitochondrial diabetes; etc. MODY refers to "Maturity onset diabetes of the young" and encompasses any of several hereditary forms of diabetes mellitus caused by mutations in an autosomal dominant gene that disrupts insulin production. MODY is often referred to as monogenic diabetes to distinguish it from the more common types of diabetes (especially type 1 and type 2), which involve more complex combinations of causes involving multiple genes and environmental factors. MODY 2 and MODY 3 are the most common forms.

Subjects may be diagnosed as in need of treatment with the compounds disclosed herein by any of several ways. Examples include but are not limited to: subjects with a glycated hemoglobin (A1C) test level of higher than 5.7%, e.g., levels between 5.7% and 6.4% are considered prediabetes and a level of 6.5% or higher on two separate tests indicates type 2 diabetes. A fasting blood sugar level from 100 to 125 mg/dL (5.6 to 7.0 mmol/L) is considered prediabetes and a fasting blood sugar level of 126 mg/dL (7.0 mmol/L) or higher indicates type 2 diabetes. An oral glucose tolerance test showing a blood sugar level from 140 to 199 mg/dL (7.8 to 11.0 mmol/L) is considered prediabetes and a blood sugar level of 200 mg/dL (11.1 mmol/L) or higher indicates type 2 diabetes. Subjects in whom one or more of these indicators is present may be treated using the compounds disclosed herein.

The agents disclosed herein may be administered in vivo by any suitable route including but not limited to: orally (e.g., capsule, solution or suspension), by injection (e.g., intraperitoneal, intradermal), etc. In preferred embodiments, the mode of administration is oral.

The amount of compound that is administered per dose is generally in the range of from about 5 to about 50 mg, such as about 5, 10, 15, 20, 25, 30, 35, 40, 45 or 50 mg per dose that is administered. However, lower and higher doses (e.g., from about 1 to about 100 mg) are also encompassed. In some aspects, the dose ranges from 0.2 mM to about 0.00625 mM. Generally, a dose is taken orally just before a meal, so on average, each dose is taken about 3 times per day. An initial low dose may be taken and the dose may be maintained or adjusted (increased or decreased), depending on how much the blood sugar level is lowered for the subject after the subject has been treated for e.g., 1-4 weeks. Continual monitoring of blood sugar levels is advised since other measures (such as lifestyle changes, weight loss, etc., as described below) may permit a lowering of the dose over time. In general, a maintenance dose may be e.g., from about 25 mg to about 50 mg orally 3 times a day, with a maximum dose being about 25 mg orally 3 times a day for a subject weighing 60 kg or less; or about 50 mg orally 3 times a day for a subject weighing more than 60 kg. The greater potency exhibited by compound 1, 3 & 4 than acarbose might be corelated to their in vitro α-glucosidase inhibitory potential with respective $IC_{50}$ values of 33.1±2.41, ($IC_{50}$=78.3±1.71) and ($IC_{50}$=116.8±1.62) than that of standard acarbose ($IC_{50}$=840±1.73). The compound concentrations are maintained the same throughout. All the compounds are always tested with same concentrations to better know the potency. Individual doses may be in the form of e.g., tablets, capsules, etc. and may be manufactured in bulk, in blister packs, or in any other suitable form. All such manufactured products are encompassed by the present disclosure.

The pharmaceutical compositions may only contain a compound as disclosed herein or may also comprise one or more other biologically active ingredients, e.g., one or more other drugs that are useful in treating high blood sugar levels, and/or the other conditions described herein. For example, metformin, acarbose, medications to control cholesterol, high blood pressure, and hyperlipidemia, etc. Other examples of compounds that may be included are described in issued U.S. Pat. No. 10,413,580, the complete contents of which is herein incorporated by reference in entirety. One or more of the present compounds may be formulated with one or more other drugs in a single dosage form, e.g., a single pill, gel capsule, etc.

In addition, administration of the compounds disclosed herein may be accompanied by other treatment measures and lifestyle changes, e.g. dietary changes to low fat, low sugar, high fiber diets; increased exercise; weight loss; smoking cessation; administration of other medications (administered separately, in a separate pill, capsule, etc.) such as metformin, acarbose, medications to control cholesterol and high blood pressure, agents listed in U.S. Pat. No. 10,413,580, etc., or any other medication commensurate with the treatment of the disease or condition that has caused or exacerbated by or is associated with the high blood sugar levels.

The subjects that are treated using the methods described herein are generally mammals and are typically humans. However, veterinary uses of the compounds are also encompassed, e.g., to treat companion pets which have diabetes. If the subject is a human, the subject may be a child or an adult, and may be e.g., over 45 years of age or older.

Various diseases and conditions are prevented and/or treated in subjects to whom the compounds disclosed herein are administered. Preventing and treating include, for example, the return of post-prandial blood sugar levels to normal. However, those of skill in the art will recognize that "preventing and treating" also encompass a lessening of symptoms (e.g., blood sugar is lowered), a slowing of symptoms (e.g., the onset of diabetes is delayed), and/or the prevention of the onset of other more serious diseases/conditions and complications thereof e.g., preventing or avoiding the progression of a condition such as pre-diabetes to full-blown diabetes, which could otherwise eventually require the administration of insulin, etc. In other words, the symptoms which prompt the initial administration may or may not be completely eradicated by treatment (the disease or condition may or may not be completely "cured"), but if not, many health benefits can still accrue for the subject.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitation, such as "wherein [a particular feature or element] is absent", or "except for [a particular feature or element]", or "wherein [a particular feature or element] is not present (included, etc.)".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Example 1.

Plant Collection

The roots of *Heterophragma adenophyllum* were obtained from the main campus University of Peshawar KP, Pakistan. The identification of plant specimens was done by Dr. Barkathulah, Assistant Prof. Department of Botany, Islamia College University, KPK, Pakistan. The voucher specimen no ICU(Bot987) was kept at the herbarium of Botany Department Islamia College University, KPK, Pakistan.

Extraction and Purification

The plant materials (Roots) were washed with water to remove clay, and then shade dried, and ground with local grinder. The powdered plant material (1.23 kg) was assessed via cold extraction by methanol (3 times). The obtained extract was concentrated at low temperature and pressure by using rotating evaporator. The crude extract was suspendered in a minimum amount of water and then treated with various solvents having different polarities to produced four fractions: hexane, dichloromethane (DCM), ethylacetate (EtOAc), and methanol. Among the fractions, the methanolic fractions comprised the maximum amount of compounds which were then subjected to column chromatography (CC) on silica gel. The column was eluted by using chloroform and methanol as a solvent system (90:10), which afforded compounds (1-4). The obtained compounds were washed with hexane to obtain pure compounds (1-4; FIG. 1). The chemical structures of the isolated compounds were identified from spectroscopic data, which shows agreement with reported data (14-16).

Structure Elucidation

Figure 2A:
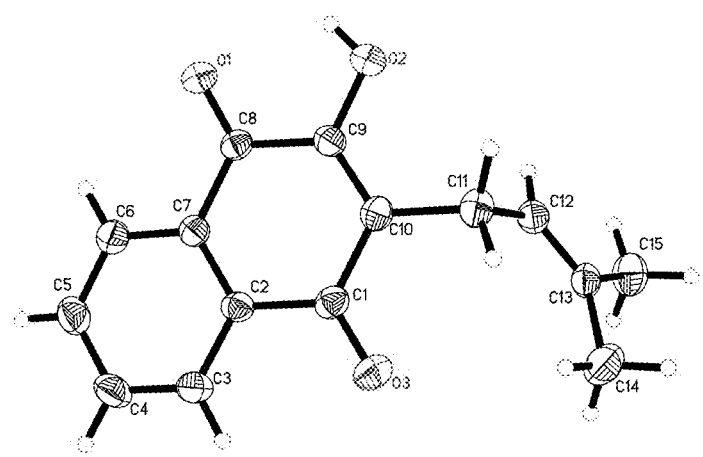
FIG. 2A and B. Single X-ray crystallography Image of A, lapachol (1) and B, peshawaraquinone (2) isolated from *H. adenophyllum*.
Figure 2B:
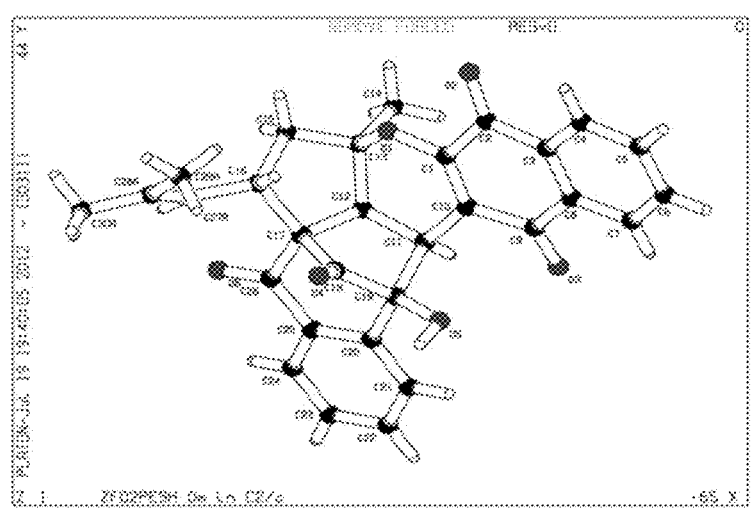

The chemical structures of the isolated phytochemicals, namely lapachol (1), peshawaraquinone (2), indanone derivatives (3) and α-lapachone (4) were elucidated recently by our group with the help of mass spec, $^1$HNMR, $^{13}$C-NMR, Heteronuclear Multiple Bond Correlation (HBMC), COSY and NOSEY spectral analysis. Furthermore, the chemical structure of two crystalline compounds lapachol (1) and peshawaraquinone (2), were confirmed by single X-ray crystallography analysis as shown in FIG. 2 (14-16).

α-glucosidase Inhibitory Activity

The α-glucosidase inhibitory activity of pure compounds lapachol (1), peshawaraquinone (2), indanone derivatives (3) and a-lapachone (4) was assessed according to standard procedure (17-19). α-glucosidase (E.C.3.2.1.20) activity was done by using 0.1 M phosphate buffer, pH 6.8 at 37° C. The α-glucosidase enzyme (0.2/ml) was incubated with different concentrations of the isolated compounds lapachol (1), peshawaraquinone (2), indanone derivatives (3) and α-lapachone (4) in buffered salines at 37° C. for 15 minutes. The substrate (0.7 Mm, p-nitrophenyl-α-d-glucopyranoside) was then mixed in and the difference in absorbance at 400 nm was recorded using a spectrophotometer for 30 minutes. The tested extracts and compound 1 were substituted with DMSO-d6 (7.5%) in the control. The standard drug used in this experiment was acarbose. The percentage activity was calculated by using the following formula.

$$\text{Percent inhibition} = 100 - \frac{OD \text{ test well}}{OD \text{ control}} \times 100$$

Molecular Docking Methodology

Molecular docking (MD) was performed using a MOE-DOCK module implemented in Molecular Operating Environment (MOE) software package [20] to dock the compounds in the active site of the α-glucosidase enzyme. Due to the unavailability of crystallographic structure of the corresponding enzyme, we used the homology modelling structural coordinates described by Carreiro et al [21] for the α-glucosidase enzyme. The three-dimensional structures of the compounds were modelled by using the Builder Module in MOE. During the molecular docking study, the compounds were set to flexible during docking, to obtain a minimal energy complex.

Results of the Invention

The discovery of new and novel drugs to cure various diseases is an ongoing process. Therefore, researchers are searching isolated natural products which have significant activity and no or low toxic effects. The present finding deals with the isolation and purification of potent α-glucosidase inhibitors from the methanolic extract of *Hetterophragma adenophyllum*. The methanolic extracts were subjected to normal phase column chromatography (CC) which yielded four compounds namely: Lapachol (1), Peshawaraquinone (2), Indanone derivatives (3), α-lapachone (4). Furthermore, the isolated compounds were evaluated for α-glucosidase inhibitory activity. All compounds exhibited α-glucosidase activity, and among the tested compounds, 1, 4 and 3 were found to have potent activity, exhibiting $IC_{50}$ values of 33.1±2.41, 78.3±1.71 and 116.8±1.62, respectively, to the standard (acarbose; $IC_{50}$=840±1.73). Compound 2 was found to be the least active. In addition to α-glucosidase activity, molecular docking analyses were performed to discover the mechanism of inhibition of the active phytochemicals. The chemical structures of isolated phytochemicals (1-4) were elucidated by advanced spectroscopic analysis and the structures of compounds 1 and 2 were confirmed by single-ray crystallographic crystallography. The identified active compounds are used e.g., for treatment of diabetes.

To investigate the potential binding mode of the phytochemicals to the α-glucosidase enzyme, the Molecular Docking (MD) method was carried out. Generally, from the post-docking analysis, it was observed that mostly the 5-hydroxycyclohex-2-ene-1,4-dione (compound-1); 2-hydroxycyclohexa-2,5-diene-1,4-dione (compound-4) and the hydroxyl group (compound-3) participated in interactions with critical residues including Glu276, Phe177, Phe157, His348, Arg212, respectively. The surface representation with the zoom-in binding site is depicted in FIG. 3A. Further MD studies showed that the binding mode is found to be well accommodated in the α-glucosidase enzyme binding site. The protein-ligand interaction (PLI) profile for the most active phytochemical (compound-1) revealed favorable residue interactions, including acidic (Asp349 and Glu276) and basic (Arg212) as shown in FIG. 3B. The PLI profile for $2^{nd}$ most active phytochemical (compound-4) revealed a hydrophobic interaction (Phe177) and a polar interaction (His348) as shown in FIG. 3C. In the case of the PLI profile for $3^{rd}$ most active phytochemical (compound-2) favorable interactions with acidic and hydrophobic residues Glu276 and Phe157 were revealed (FIG. 3D). These results delineated that primarily the oxygen of 5-hydroxycyclohex-2-ene-1,4-dione and 2-hydroxycyclohexa-2,5-diene-1,4-dione moieties participated in binding and adopted favorable interactions with key residues which might have a role in enhancing enzymatic activity.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

We claim:

1. A method of inhibiting α-glucosidase, comprising:
    contacting the α-glucosidase in vitro with the following compound: methyl 1,2-dihydroxy-2-(3-methylbut-2-enyl)-3-oxo-2,3-dihydroxo-1H-indene-1-carboxylate, wherein said compound is purified to 90-100% purity.

2. A method of stabilizing or decreasing blood sugar levels in a subject in need thereof, comprising:
    administering a therapeutically effective amount of the following compound: methyl 1,2-dihydroxy-2-(3-methylbut-2-enyl)-3-oxo-2,3-dihydroxo-1H-indene-1-carboxylate, wherein the compound is in a pharmaceutically acceptable form and has a purity of 90-100%, and wherein the compound is administered multiple times.

3. The method of claim 2, wherein the therapeutically effective amount is 0.2 mM to 0.00625 mM.

4. The method of claim 2, wherein the step of administering is performed orally.

5. A method of treating diabetes mellitus in a subject in need thereof, comprising:
    administering to a subject in need thereof 1 to 100 mg of the following compound: methyl 1,2-dihydroxy-2-(3-methylbut-2-enyl)-3-oxo-2,3-dihydroxo-1H-indene-1- carboxylate, wherein the compound is in a pharmaceutically acceptable form and has a purity of 90-100%, and wherein the compound is administered multiple times.

6. The method of claim 5, wherein the step of administering is performed orally.

7. The method of claim 5, wherein the diabetes is type I diabetes, type II diabetes, secondary diabetes mellitus, gestational diabetes mellitus, or a combination of two or more of these.

8. The method of claim 5 wherein the administering step is performed a plurality of times during a day.

9. The method of claim 8 wherein 25 to 50 mg is administered 3 times per day.

\* \* \* \* \*

UNITED STATES PATENT AND TRADEMARK OFFICE
CERTIFICATE OF CORRECTION

| | | |
|---|---|---|
| PATENT NO. | : 11,452,708 B2 | Page 1 of 1 |
| APPLICATION NO. | : 17/169666 | |
| DATED | : September 27, 2022 | |
| INVENTOR(S) | : A Rauf et al. | |

It is certified that error appears in the above-identified patent and that said Letters Patent is hereby corrected as shown below:

On the Title Page

Item (72) Please correct the residence information for the following inventors:
1) Abdur Rauf, Swabi (PK)
2) Zafar Ali Shah, Peshawar (PK)
4) Abdul Wadood, Mardan (PK)

Signed and Sealed this
Twenty-ninth Day of November, 2022

Katherine Kelly Vidal
*Director of the United States Patent and Trademark Office*